United States Patent [19]
Arai et al.

[11] Patent Number: 5,755,672
[45] Date of Patent: May 26, 1998

[54] MEASURING EQUIPMENT OF FAT AND WATER AMOUNT EXISTING ON THE OBJECT

[75] Inventors: Junichi Arai; Makoto Toyota, both of Urawa, Japan

[73] Assignee: Moritex Corporation, Japan

[21] Appl. No.: 665,678

[22] Filed: Jun. 18, 1996

[30] Foreign Application Priority Data

Nov. 30, 1995 [JP] Japan .................... 7-313027

[51] Int. Cl.[6] .................................. A61B 5/00
[52] U.S. Cl. .................. 600/547; 600/572; 324/696; 356/70
[58] Field of Search .................. 128/632, 757, 128/759, 760, 734, 743, 744, 749; 324/692, 694, 696, 722; 250/301; 356/70; 73/53.01; 600/309, 372, 547, 556, 557, 562, 570, 572, 573

[56] References Cited

U.S. PATENT DOCUMENTS

| | | | |
|---|---|---|---|
| 4,494,554 | 1/1985 | Van Dyke et al. | 128/734 |
| 4,494,869 | 1/1985 | Neumann | 356/70 |
| 4,623,793 | 11/1986 | Hofke et al. | 128/759 |
| 4,966,158 | 10/1990 | Honma et al. | 324/692 |
| 5,001,436 | 3/1991 | Scot et al. | 324/692 |
| 5,433,214 | 7/1995 | Brehm et al. | 128/760 |

FOREIGN PATENT DOCUMENTS

| | | |
|---|---|---|
| 226738 | 1/1990 | Japan . |
| 326230 | 2/1991 | Japan . |

*Primary Examiner*—Jennifer Bahr
*Assistant Examiner*—Eric F. Winakur
*Attorney, Agent, or Firm*—Brown, Martin, Haller & McClain LLP

[57] ABSTRACT

Making a measurement device that measures the water content and oil content of the skin into a portable size such that a female beautician can put it in a bag and easily carry it. Because a freely detachable oil content sample cap can be mounted so that it fits onto a measurement probe on the tip of which has been arranged a water content sensor to detect the amount of water on the surface of the sample under examination, when measuring the amount of water content, the water content sensor on the tip of the measurement probe may be pressed onto the surface of the sample under examination as is, or, when measuring the amount of oil content, after sampling the oil content by mounting an oil content sample cap on the tip of the measurement probe, that oil content sample cap may be removed from the measurement probe and inserted into an oil content measurement hole, and therefore, a water content measurement device and an oil content measurement device may be jointly used with a single measurement probe, and consequently, it is not necessary to provide multiple probes, and the device can be made small-scale.

3 Claims, 3 Drawing Sheets

MEASURING EQUIPMENT OF FAT AND WATER AMOUNT EXISTING ON THE OBJECT

BACKGROUND OF THE INVENTION

1. Field of the Invention

The present invention is related to an oil and water content measurement device to measure the amount of oil content and the amount of water content adhering to the surface of the sample under examination, and in particular, the present invention is applied to the measurement of the amount of skin oil (amount of oil content) and the amount of water content adhering to the surface of skin.

2. Description of the Related Art

This kind of oil and water content measurement device to measure the amount of skin oil and amount of water content of skin is used for the purpose of obtaining reference data when selecting the most suitable cosmetic corresponding to the characteristics of the skin of the customer at stores such as cosmetic sales locations. (Refer to Patent Disclosure No. Hei 2-26738, and Patent Disclosure No. Hei 3-26230).

FIG. 3 is a perspective diagram indicating this kind of conventional oil and water measurement device; FIG. 4 is a block diagram of this, and holders 57, 58 and 59 are formed on the upper surface of table top type device main body 50 to receive respectively, oil content measurement probe 52 on the tip of which oil content sample cap 51 can be mounted, amount of water content measurement probe 52 on the tip of which water content sensor 53 is arranged, and skin temperature measurement probe 56 on the tip of which temperature sensor 55 is arranged. Oil content measurement optical system 61, which irradiates oil content sample cap 51 with light and detects the intensity of the reflected light, is arranged on the bottom part of holder 57 which receives the aforementioned oil content measurement probe 52, and aforementioned amount of water content measurement probe 54 and skin temperature measurement probe 56 are connected to device main body 50 through signal lines 62 and 63.

Inside of device main body 50 are provided: amount of oil content measurement means 64, which measures the amount of oil content based on the intensity of reflected light that is detected by aforementioned oil content measurement optical system 61; amount of water content measurement means 65, which calculates the amount of water based on the output signal of water content sensor 53; and temperature measurement means 66, which calculates the skin temperature based on the output signals of temperature sensor 55. On the front surface of device main body 50 are provided: amount of oil content display part 67, amount of water content display part 68, and temperature display part 69, which display respectively the amount of oil content, the amount of water content, and the skin temperature calculated by the aforementioned measurement means 64, 65, and 66.

First, when measuring the amount of oil content, oil content sample cap 51 is mounted on the tip of oil content measurement probe 52, and the intensity of reflected light prior to oil content sampling is measured. Afterwards, oil content measurement probe 52 is removed from holder 57, and oil content sample cap 51 is pressed onto the skin. After sampling the oil, oil content measurement probe 52 is again received inside of holder 57, the intensity of reflected light after sampling the oil content is measured, and the amount of oil content measured based on the changes of the intensity of that reflected light is displayed on oil content display part 67.

Next, when measuring the amount of water content, water content measurement probe 54 is removed from holder 58, and water content sensor 53, which is the tip, is pressed onto the skin. When switch 54a is pressed, the amount of water content is calculated by the water content measurement means based on those output signals, and the results are displayed on water content display part 68.

Further, the skin temperature can be measured in the same way as the amount of water content using temperature measurement probe 56.

SUMMARY OF THE INVENTION

Nonetheless, this kind of oil and water content measurement device requires measurement probes 52 and 54 for each targeted measurement such as water content, and therefore, there is the problem that, inevitably, the device main body is made into a table top type, and it becomes large scale.

Consequently, the device may be used by normal installation in a store front, but for example, if a visiting salesman uses it as a tool for promoting sales, or if a beautician for a cosmetics manufacturer responsible for multiple sales outlets must carry it around, the device is too large scale to carry, and it is inconvenient to handle.

Also, if measuring oil content, the time of holding the oil content sample tip onto the skin is not fixed, and there is the problem of large measurement errors.

Thus, the present invention takes up the technical issues of, firstly, making the device extremely small-scale and forming it compactly such that even a female beautician can easily put it in a bag and carry it, and secondly, when the oil content is measured, there is very little error no matter who does the measurement.

In order to solve these issues, the present invention is an oil and water content measurement device to measure the amount of oil content and the amount of water content adhering to the surface of the sample under examination, and provides a measurement probe on the tip of which is arranged a water content sensor to measure the amount of water content on the surface of the sample under examination, and also provides an amount of water content measurement means to calculate the amount of water content based on the output signals of the aforementioned water content sensor. In addition, the invention is characterized by providing: a freely detachable oil content sample cap which is mounted on the tip of the aforementioned measurement probe such that it covers the aforementioned water content sensor; an oil content measurement hole inside of which is arranged an oil content detection optical system that irradiates the oil content sample surface of the oil content sample cap with light and detects the amount of that reflected light; an amount of oil content measurement means which calculates the amount of oil content based on the output signals of the aforementioned oil content detection optical system; and a display part to display the amount of water content and the amount of oil content calculated by the aforementioned amount of water content measurement means and the amount of oil content measurement means.

According to this, when measuring the amount of water content, the measurement probe may be pressed onto the surface of the sample under examination, or when measuring the amount of oil content, after sampling the oil content by mounting the oil content sample cap onto the tip of the measurement probe, that oil content sample cap may be removed from the measurement probe and inserted into the oil content measurement hole, and therefore, the device which measures the water content with a measurement probe and the device which measures the oil content can be combined into one device, and consequently it is not necessary to provide multiple probes, and the device can be made small-scale.

Also, according to a more suitable form of embodiment, a switching sleeve on the tip of which the aforementioned water content sensor is attached is supported such that it can slide, and a switch is provided which is manipulated when the aforementioned switching sleeve is pressed into the measurement probe. Said switch is made such that, during amount of water content measurement, switch signals are output which activate the amount of water content measurement means when the water content sensor is pressed onto the sample under examination; and during amount of oil content measurement, switch signals are output which drive the timer to sound a warning when a fixed amount of time has elapsed after the oil content sample cap has been pressed onto the sample under examination.

According to this, when the tip of the measurement probe is pressed onto the surface of the sample under examination, the switch is manipulated by pressing the switching sleeve in, and therefore during amount of water content measurement, switch signals which activate the amount of water content measurement means are output when the water content sensor is pressed onto the sample under examination; and during amount of oil content measurement, switch signals which drive the timer that sounds the warning when a fixed time has elapsed are output after pressing the oil content sample cap onto the sample under examination.

Specifically, when the oil content sample cap that has been mounted on the tip of the measurement probe is pressed onto the surface of the sample under examination, the switch is manipulated by the switching sleeve being pressed in, the timer is activated, and a warning sound is issued after a fixed time (for example, 10 seconds) has elapsed. Therefore, the time that the oil content sample cap is pressed onto the surface of the sample under examination is kept fixed, and it is possible to have hardly any measurement error caused on the oil content sampling time being too long or too short.

According to an even more suitable shape of embodiment, the aforementioned measurement probe, aforementioned amount of water content measurement means, the aforementioned oil content measurement content, the aforementioned amount of oil content measurement means and the aforementioned display part are arranged on the device main body of the oil and water content measurement device to form an all-in-one type, and an even more compact device can be formed.

BRIEF DESCRIPTION OF THE DRAWINGS

Below, the present invention will be concretely explained based on the forms of embodiment indicated in the diagrams.

DESCRIPTION OF THE PREFERRED EMBODIMENTS

Figure 1:
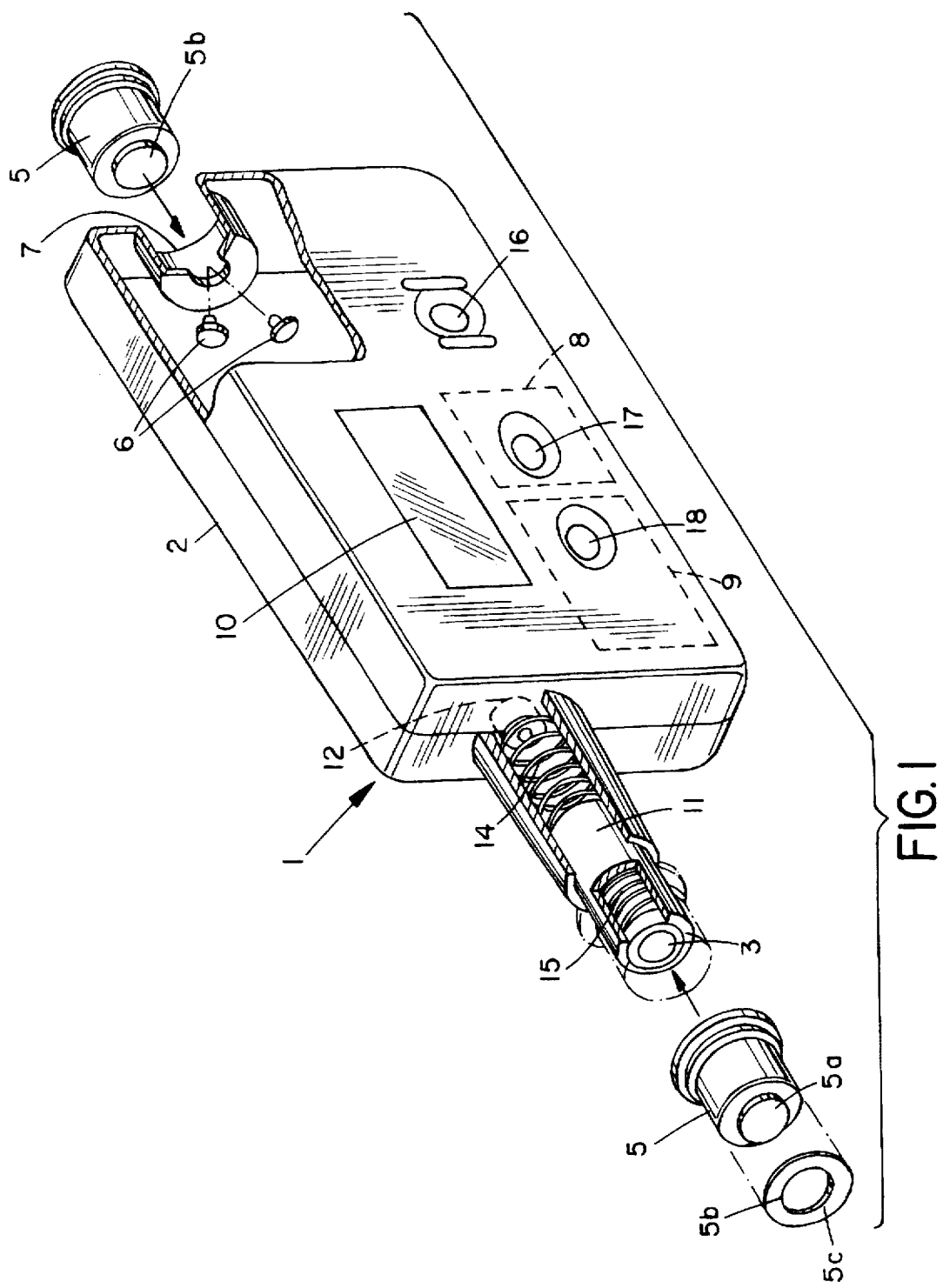
FIG. 1 a perspective diagram indicating one example of an oil and water content measurement device relating to the present invention.
Figure 2:
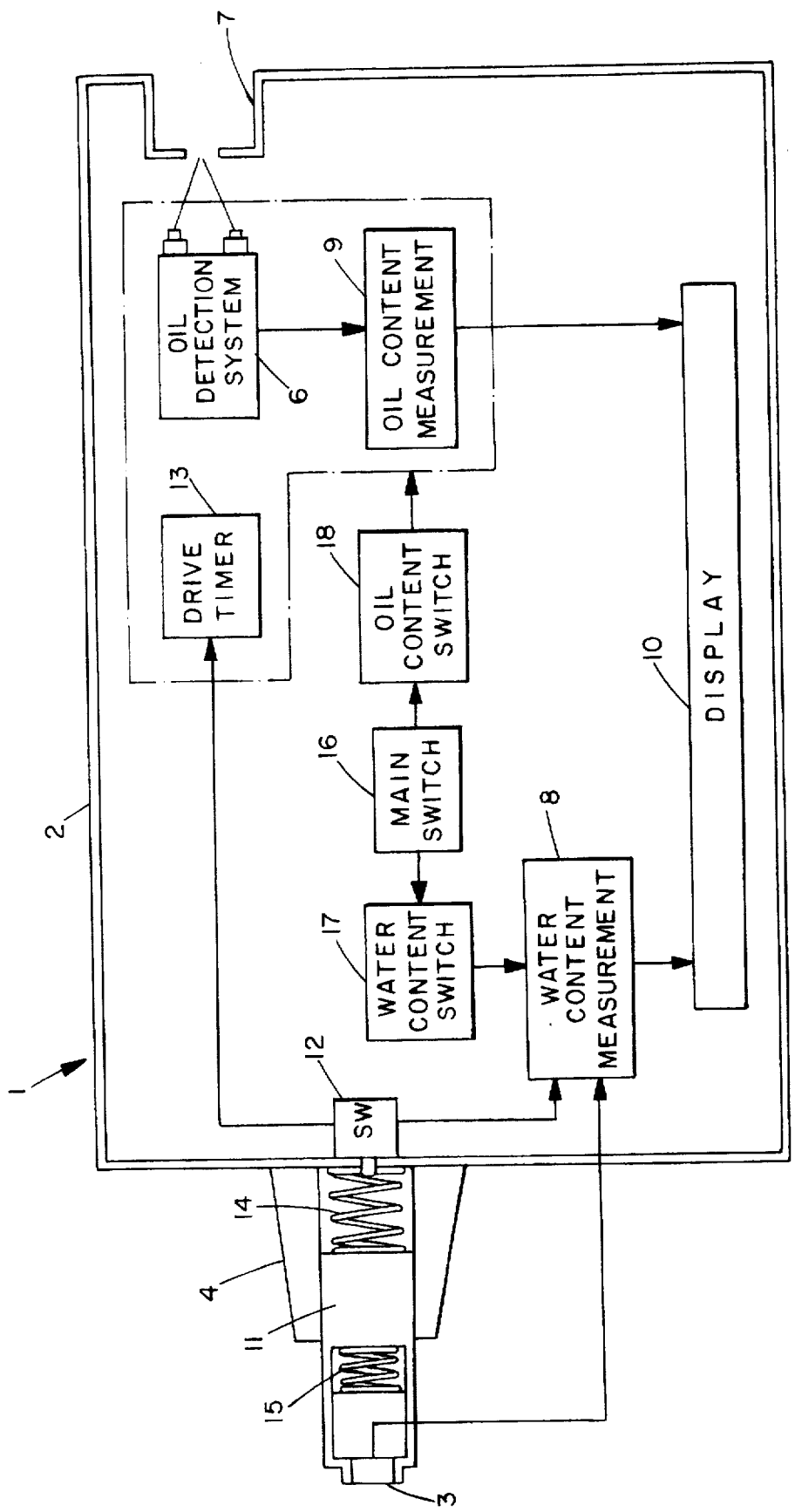
FIG. 2 is a block diagram of the same.
Figure 3:
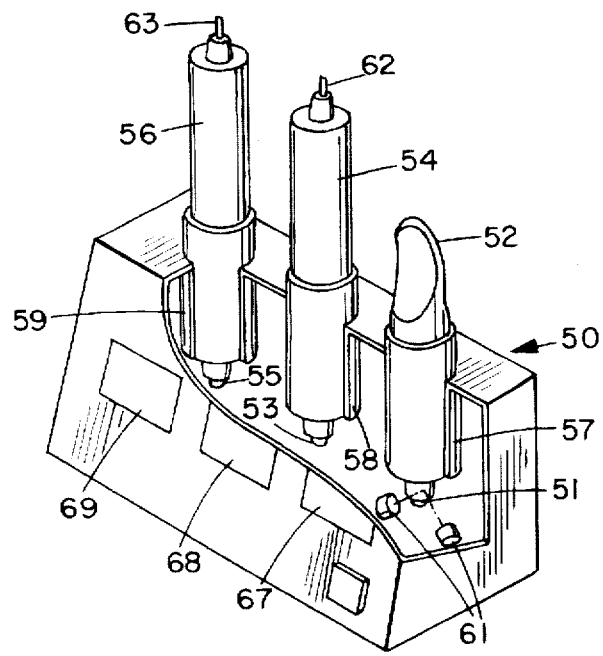
FIG. 3 is a perspective diagram indicating a conventional device.
Figure 4:
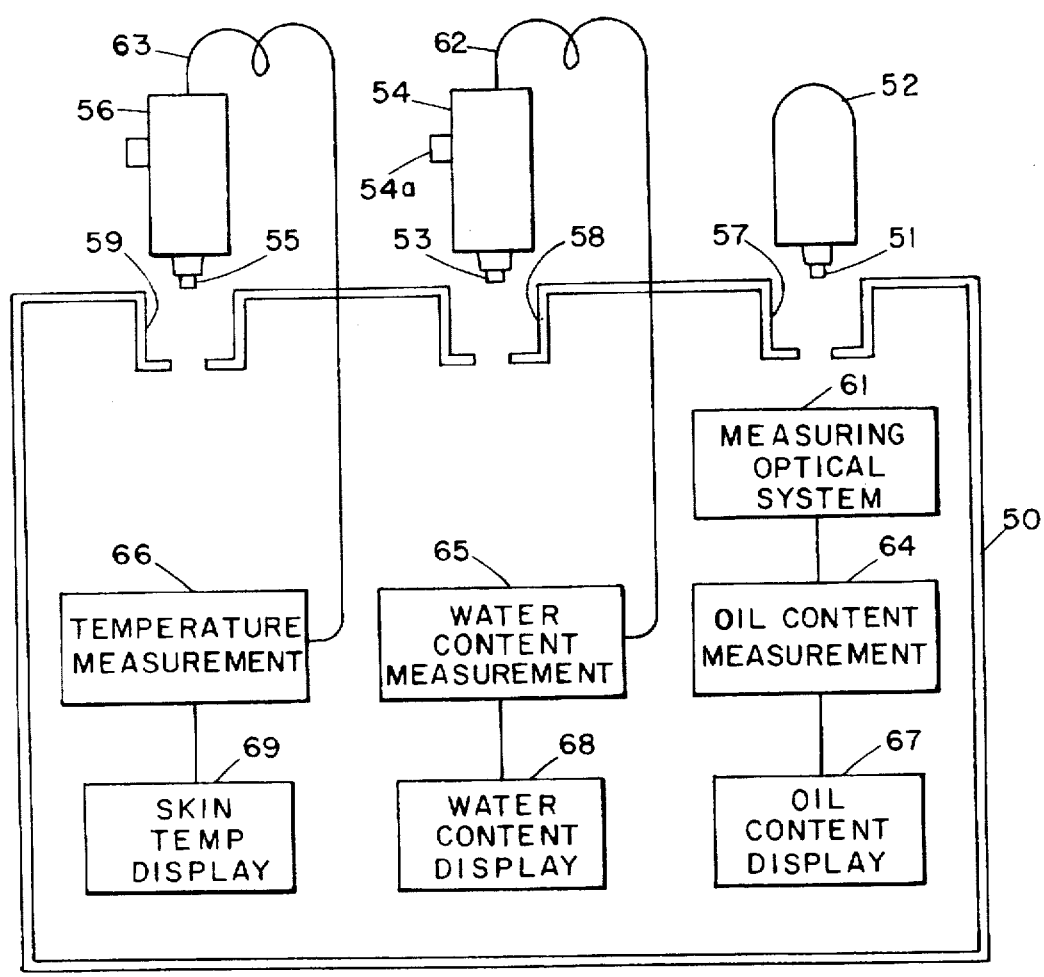
FIG. 4 is a block diagram of a conventional device.

In the diagram, 1 is the oil and water content measurement device to measure the amount of oil content and the amount of water content adhering to the surface of the sample under examination; measurement probe 4 on the tip of which water content sensor 3 to detect the amount of water content on the surface of the sample under examination has been arranged is formed by sticking out from device main body 2 of the aforementioned oil and water content measurement device; and oil content measurement hole 7, inside of which is arranged oil content detection optical system 6 which irradiates oil content sample surface 5a of oil content sample cap 5 with light and detects the reflected light thereon, is formed on the back side of device main body 3 in relation to aforementioned measurement probe 4.

Also, amount of water content measurement means 8 which calculates the amount of water content based on the output signals of aforementioned water content sensor 3 and amount of oil content measurement means 9 which calculates the amount of oil content based on the output signals of aforementioned oil content detection optical system 6 are arranged inside of device main body 2; and display part 10 which displays the amount of water content and the amount of oil content calculated by aforementioned amount of water content measurement means 8 and amount of oil content measurement means 9 is arranged on the front surface of device main body 2.

In addition, an electrostatic variable capacity sensor that detects the amount of water content based on the electrostatic capacity of the sample under examination which is touched by the measurement surface may, for example, be used as water content sensor 3, and an electrostatic capacity—amount of water content conversion table in which is memorized the relationship between the size of electrostatic capacity and the amount of water content is held in the memory of aforementioned amount of water content measurement means 8.

Oil content sample cap 5 is configured such that affixed to it is seal 5b on which paint for which the light reflection rate changes depending on the amount of adhering oil content is painted on oil content sample surface 5a on its tip; it is freely detachable and mounted onto the tip of aforementioned measurement probe 4 such that aforementioned water content sensor 3 is covered; is pressed onto the surface of the sample under examination in a state of having been mounted on the tip of measurement probe 4 during oil content measurement; after sampling the oil content on the surface of the sample under examination, said cap 5 is removed from measurement probe 4; and by inserting into aforementioned oil content measurement hole 7, the amount of oil content is optically measured.

The intensity of reflected light when the oil content is not adhering to seal 5b is memorized as amount of oil content 0 by amount of oil content measurement means 9, and a reflected light intensity—amount of oil content conversion table which holds the relationship between the reflected light intensity and the amount of oil content was placed in memory ahead of time.

Furthermore, the paint surface of seal 5b is covered by overlay 5c such that oil on the fingers will not adhere onto the surface when affixing this, and after having been affixed onto oil content sample surface 5a of oil content sample cap 5 with overlay 5c attached as is, the device is used by peeling off just overlay 5c. Also, after use, it may be used again by replacing seal 5b only, but if necessary, this kind of paint may be coated on oil content sample surface 5a in advance, and oil content sample cap 5 may be used once and thrown away.

Moreover, switching sleeve 11, on the tip of which aforementioned water content sensor 3 is attached, is supported on measurement probe 4 such that it can slide, and also provided is switch 12 which is manipulated when aforementioned switching sleeve 11 is pressed in.

During amount of water content measurement, this switch 12 outputs switch signals to activate amount of water content measurement means 8 when water content sensor 3 is pressed onto the surface of the sample under examination and switching sleeve 11 is pressed in. Also, during amount of oil content measurement, this switch 12 is configured to output switch signals that drive timer 13 when measurement probe 4 with oil content sample cap 5 mounted is pressed onto the sample under examination and switching sleeve 11 is pressed in; and said timer 13 is configured such that a warning tone will sound after a fixed time has elapsed once the switch signal has been entered.

In addition, 14 is a spring which energizes switching sleeve 11 in the expansion direction, and is built into measurement probe 4; 15 is a spring by which water content sensor 3 is pressed onto the sample under examination with a fixed force, and is built into switching sleeve 11.

Also, 16 is the main switch, 17 is the amount of water content measurement switch, and 18 is the amount of oil content measurement switch.

The above is one configuration of the present invention, and its use will be explained next.

First, when attempting to measure the amount of water content, after main switch 16 has been pressed, when amount of water content measurement switch 17 is pressed, device main body 2 is held in the hands, and water content sensor 3 which is attached to the tip of measurement probe 4 is pressed onto the surface of the sample under examination, switching sleeve 11 is pressed inside of measurement probe 4, and switch signals to activate amount of water content measurement means 8 are output from switch 12.

Amount of water content measurement means 8 measures the electrostatic capacity of the sample under examination based on the detection signals that are output from water content sensor 3, reference is made to the electrostatic capacity—amount of water content conversion table based on this, and the amount of water content is displayed on display part 10 by substituting in a graded numerical value such as, for example, 1–15.

Next, when attempting to measure the amount of oil content, seal 5b is affixed on oil content sample surface 5a of oil content sample cap 5, overlay 5c is peeled off, and cap 5 is mounted on the tip of measurement probe 4 such that it covers water content sensor 3.

Then, amount of oil content measurement switch 18 is pressed this time, and when oil content sample cap 5 which has been mounted onto the tip of measurement probe 4 is pressed onto the surface of the sample under examination, switching sleeve 11 is pressed inside of measurement probe 4, and switch signals to activate timer 13 are output from switch 12.

When switch signals are entered, timer 13 gives a beeping warning sound after a fixed amount of time has elapsed (for example, after 10 seconds have elapsed), and therefore the time of pressing oil content sample cap 5 onto the sample under examination can always be kept constant, and measurement errors caused by the time of pressing on being too long or too short can be eliminated.

Next, oil content sample cap 5 is removed from measurement probe 4, and inserted into oil content measurement hole 7. At this time, oil content measurement optical system 6 has already been lit at the point in time when amount of oil content measurement switch 18 was pressed, and the intensity of that reflected light is detected.

Meanwhile, oil content measurement means 9 is such that it automatically begins calculations when reflected light at a fixed level or above has entered, and when oil content sample cap 5 is inserted into oil content measurement hole 7, calculation of the amount of oil content is begun because reflected light of a fixed level (or above) is detected.

Then, when the intensity of reflected light of oil content sample surface 5a of oil content sample cap 5 is detected, reference is made to the reflected light intensity—amount of oil content conversion table based on this, and the amount of oil content is displayed on display part 10 by substituting in a graded numerical value such as, for example, 1–15.

As described above, according to the present invention, because a device for measuring water content and a device for measuring oil content are combined in a single measurement probe, one measurement probe is sufficient, and it is not necessary to utilize multiple measurement probes. Consequently, it is possible to make the overall device small-scale. Because there is just one probe, an all-in-one type device which is attached to the main body of the device can be made, and thus there is the greatly superior effect of being able to plan an even more compact device.

Also, when pressing the tip of the measurement probe on the surface of the sample under examination, the switch is manipulated by pressing in the switching sleeve. During amount of water content measurement, switch signals to activate the amount of water content measurement means are output when the water content sensor is pressed onto the sample under examination, and also, during amount of oil content measurement, switch signals to activate a timer which sounds a warning tone after a fixed amount of time has elapsed are output once the oil content sensor cap has been pressed onto the sample under examination. Therefore, there are the effects that the time that the oil content sample cap is pressed onto the surface of the sample under examination can be kept fixed, measurement errors caused by the time of taking the oil content sample being too long or too short can be eliminated, and accurate measurement can be conducted.

Although preferred embodiments of the present invention have been described above by way of example only, it will be understood by those skilled in the field that modifications may be made to the disclosed embodiments without departing from the scope of the invention, which is defined by the appended claims.

We claim:

1. An oil and water content measurement device for measuring the amount of oil and the amount of water adhering to the surface of a specimen under examination, the device comprising:

a main body;

a measurement probe projecting from said main body and having a tip, a water content sensor arranged on the tip of said probe for detecting the amount of water content on the surface of a specimen under examination, the water content sensor having an output signal dependent on said amount of water content, and a means for measuring the amount of water content which calculates the amount of water content based on the output signal of said water content sensor;

an oil sample cap detachably mounted on the tip of said measurement probe such that it covers said water content sensor, said oil sample cap having an oil content sampling surface;

the main body having an oil content measurement hole for removably receiving said oil sample cap after collection of a sample, an oil content detection optical system positioned in said main body adjacent said oil content measurement hole for irradiating with light the oil content sampling surface of the oil sample cap and detecting light reflected from said oil content sampling surface, the oil content detection optical system having output signals dependent on the amount of reflected light detected, and an amount of oil content measuring means for calculating the amount of oil content based on the output signals of said oil content detection optical system; and a display part for displaying the amount of water content and the amount of oil content calculated by said amount of water content measurement means and said amount of oil content measuring means.

2. The oil and water content measurement device as claimed in claim 1 in which said amount of water content measurement means, said amount of oil content measurement means, and said display part are arranged on the main body of the device.

3. An oil and water content measurement device for measuring the amount of oil and the amount of water adhering to the surface of a specimen under examination, the device comprising:

a main body:

a measurement probe projecting from said main body and having a tip, a water content sensor arranged on the tip of said probe for detecting the amount of water content on the surface of a specimen under examination, the water content sensor having an output signal dependent on said amount of water content, and a means for measuring the amount of water content which calculates the amount of water content based on the output signal of said water content sensor;

an oil sample cap detachably mounted on the tip of said measurement probe such that it covers said water content sensor, said oil sample cap having an oil content sampling surface;

the main body having an oil content measurement hole for removably receiving said oil sample cap after collection of a sample, an oil content detection optical system positioned in said main body adjacent said oil content measurement hole for irradiating with light the oil content sampling surface of the oil sample cap and detecting light reflected from said oil content sampling surface, the oil content detection optical system having output signals dependent on the amount of reflected light detected, and an amount of oil content measuring means for calculating the amount of oil content based on the output signals of said oil content detection optical system;

a display part for displaying the amount of water content and the amount of oil content calculated by said amount of water content measurement means and said amount of oil content measuring means; and a switching sleeve slidably mounted on said measurement probe for movement between extended and retracted positions and attached to said water sensor;

a switch in said main body positioned for activation when the switching sleeve is pressed into said retracted position;

wherein, during amount of water measurement, switch signals are output to activate the amount of water content measurement means when the water content sensor is pressed onto the sample under examination; and a timer for producing a warning sound when a fixed amount of time has elapsed after activation of the timer;

said switch further comprising means for producing switch signals for activating said timer during amount of oil content measurement when the oil sample cap is pressed onto the specimen under examination.

* * * * *